United States Patent
Hirschman

(10) Patent No.: US 7,465,711 B2
(45) Date of Patent: Dec. 16, 2008

(54) TREATMENT OF CANCERS OF LYMPHOCYTIC CELLS WITH PRODUCT R

(75) Inventor: Shalom Z Hirschman, Riverdale, NY (US)

(73) Assignee: Advanced Viral Research Corporation, Yonkers, NY (US)

( * ) Notice: Subject to any disclaimer, the term of this patent is extended or adjusted under 35 U.S.C. 154(b) by 6 days.

(21) Appl. No.: 11/704,393

(22) Filed: Feb. 8, 2007

(65) Prior Publication Data

US 2007/0207969 A1 Sep. 6, 2007

Related U.S. Application Data

(62) Division of application No. 10/446,895, filed on May 28, 2003, now abandoned.

(60) Provisional application No. 60/383,639, filed on May 28, 2002.

(51) Int. Cl.
A61K 38/00 (2006.01)

(52) U.S. Cl. ....................................................... 514/21

(58) Field of Classification Search ................ None
See application file for complete search history.

(56) References Cited

U.S. PATENT DOCUMENTS

| | | | |
|---|---|---|---|
| 5,807,839 A | 9/1998 | Hirschman | |
| 5,807,840 A | 9/1998 | Hirschman | |
| 5,849,196 A | 12/1998 | Kochel | |
| 5,902,786 A | 5/1999 | Bregman | |
| 6,268,349 B1 | 7/2001 | Hirschman | |
| 6,303,153 B1 | 10/2001 | Friedland et al. | |
| 6,312,602 B1 | 11/2001 | Kochel | |
| 6,355,226 B1 | 3/2002 | Hirschman | |
| 6,440,658 B1 | 8/2002 | Huang et al. | |
| 6,528,098 B2 | 3/2003 | Friedland et al. | |
| 6,670,118 B2 | 12/2003 | Hirschman | |
| 6,696,422 B2 | 2/2004 | Hirschman | |
| 6,921,542 B2 | 7/2005 | Friedland et al. | |
| 7,067,139 B2 | 6/2006 | Hirschman | |
| 7,074,767 B2 | 7/2006 | Friedland et al. | |
| 2001/0006682 A1 | 7/2001 | Hirschman | |
| 2001/0049351 A1 | 12/2001 | Hirschman | |
| 2002/0055483 A1 | 5/2002 | Watanabe et al. | |
| 2002/0081627 A1 | 6/2002 | Hirschman | |
| 2002/0107184 A1 | 8/2002 | Hirschman | |
| 2003/0206962 A1 | 11/2003 | Hirschman | |
| 2004/0033244 A1 | 2/2004 | Hirschman | |

OTHER PUBLICATIONS

Notice of Allowance corresponding to U.S. Appl. No. 10/456,668 dated Apr. 30, 2007.
Notice of Allowance corresponding to U.S. Appl. No. 10/456,668 dated Jun. 6, 2008.
Official Communication corresponding to U.S. Appl. No. 10/466,895 dated Aug. 9, 2006, Sep. 11, 2008.
Official Communication corresponding to U.S. Appl. No. 10/456,668 dated Jun. 28, 2006.
Official Communication corresponding to U.S. Appl. No. 10/456,668 dated Oct. 10, 2007.
Official Communication corresponding to U.S. Appl. No. 10/559,690 dated Jun. 26, 2008.

*Primary Examiner*—Cecilia J Tsang
*Assistant Examiner*—Marcela M Cordero Garcia
(74) *Attorney, Agent, or Firm*—Jenkins, Wilson, Taylor & Hunt, P.A.

(57) ABSTRACT

A method of treating a patient suffering from cancers of lymph cells such as acute lymphocytic leukemia, chronic lymphocytic leukemia, Hodgkin's disease and non-Hodgkin's lymphoma comprises parenterally administering to said patient an effective acute lymphocytic leukemia treatment amount of Product R in a pharmaceutically acceptable formulation.

9 Claims, No Drawings

TREATMENT OF CANCERS OF LYMPHOCYTIC CELLS WITH PRODUCT R

RELATED APPLICATION

This application is a divisional of U.S. patent application Ser. No. 10/446,895, filed May 28, 2003, now abandoned herein incorporated by reference in its entirety, which claims priority from the provisional application Ser. No. 60/383,639, filed May 28, 2002. The contents of provisional application Ser. No. 60/383,639 are incorporated by reference in their entirety.

BACKGROUND OF THE INVENTION

1. Field of the Invention

Present invention relates to a method of treating patients suffering from cancers of lymphocytic cells such as acute lymphocytic leukemia, chronic lymphocytic leukemia, Hodgkin's disease and non-Hodgkin's lymphoma with Product R, a peptide-nucleic acid preparation by administering Product R to the patients.

2. Related Art

Cancers of lymphocytic cells including acute lymphocytic leukemia, chronic lymphocytic leukemia, Hodgkin's disease and non-Hodgkin's lymphoma are common forms of cancer. The American Cancer Society estimates that 60,900 cases of lymphoma will occur in the U.S. in the year 2002, comprising 7,000 cases of Hodgkin's disease and 53,900 cases of non-Hodgkin's lymphoma. These cancers are estimated to cause a total of 25,800 deaths in the U.S. in the year 2002. It is estimated that 30,800 new cases of leukemia will occur in the U.S. in the year 2002 and that 21,700 patients will die with leukemia in 2002.

Although there have been significant strides in the treatment of these cancers in the past two decades, many patients still succumb to these diseases. Even in childhood lymphocytic leukemia where the results have been improving in terms of prolonging the life of the patient, and in achieving 5 year cures, approximately 15% of children still succumb to the disease with present chemotherapeutic agents.

Therefore, it is evident that new and effective agents to treat these cancers are sorely needed. Product R is a peptide-nucleic acid preparation that has broad effects on immune functions. Product R can stimulate pro-inflammatory responses when necessary such as in patients with viral infections or cancers. When an aberrant immune response already exists as in patients with autoimmune disorders such as rheumatoid arthritis, Product R will turn off the aberrant immune response thereby relieving the symptoms of the disease.

In the laboratory, Product R stimulates the synthesis of a variety of chemokines and cytokines. These include interleukin 1, interleukin 6, interleukin 8, MCP-1, interferon gamma and tumor necrosis factor alpha. In macrophages that are maximally activated in cell culture Product R will turn off the synthesis of proinflammatory cytokines and chemokines.

Product R has been used for treating many viral infections or diseases related to immune system disorders. Some of the uses of Product R are disclosed in the U.S. Pat. Nos., 6,268, 349, 6,355,226, 5,902,786, 5,807,839 and U.S. Pat application Ser. Nos., 09/189,172, 08/838,134, 08/839,651, 09/316, 374, 08/964,250, 09/705,618, 09/706,305, 09/257,739 and 09/948,221, which are incorporated by reference in their entirety.

However, Product R has never been tested or suggested to be used in patients who suffer from non-solid tumors such as Lymphocytic Leukemias, Hodgkin's Disease and Non-Hodgkin's Lymphoma. Thus, an object of the present invention is to provide a method for treating patients having non-solid tumors such as Lymphocytic Leukemias, Hodgkin's Disease and Non-Hodgkin's Lymphoma by administering Product R to such patients.

SUMMARY OF THE INVENTION

An object of the present invention is to provide a method of treating a patient suffering from cancers of lymphocytic cells such as acute lymphocytic leukemia, chronic lymphocytic leukemia, Hodgkin's disease and non-Hodgkin's lymphoma, which comprises parenterally administering to said patient an effective acute lymphocytic leukemia treatment amount of Product R in a pharmaceutically acceptable formulation.

Another object of the present invention is to provide a method of shrinking enlarged lymph nodes in patients with Hodgkin's disease or Non-Hodgkin's lymphoma, which comprises parenterally administering to said patient an effective amount of Product R for shrinking lymph node in a pharmaceutically acceptable formulation.

A further object of the present invention is to provide a method of shrinking enlarged spleen in patients with Hodgkin's disease or Non-Hodgkin's lymphoma, which comprises parenterally administering to said patient an effective amount of Product R for shrinking lymph node in a pharmaceutically acceptable formulation.

Still, a further object of the present invention is to provide a method of treating body wasting, lose of appetite and fatigue in patients suffering from acute lymphocytic leukemia, chronic lymphocytic leukemia, Hodgkin's disease and non-Hodgkin's lymphoma, which comprises parenterally administering to said patient an effective acute lymphocytic leukemia treatment amount of Product R in a pharmaceutically acceptable formulation

DETAILED DESCRIPTION AND PREFERRED EMBODIMENT OF THE INVENTION

Product R is a product developed and manufactured by Advanced Viral Research Corp. (Yonkers, N.Y.). The manufacturing process, composition, and chemical, physical and some biological properties of Product R are described in U.S. Pat. Nos. 6,303,153 and 6,528,098, the content of which is incorporated by reference in its entirety.

Product R has been found to be effective in the treatment of cancers emanating from lymphocytic cells including patients with acute lymphocytic leukemia, Hodgkin's lymphoma and non-Hodgkin's lymphoma.

According to the present invention, Product R is preferably administered to the patient parenterally, while other administration routes such as nasal spray or ingestion may also be employed. A suitable effective dose of Product R will be in the range of from about 5 microliters to about 40 microliters per kilogram of body weight per day, preferably in the range of about 10 microliters to about 25 microliters per kilogram of body weight per day. Most preferably Product R is administered in an amount of about 30 microliters per kilogram of body weight per day for about one week, followed by about 15 microliters per kilogram of body weight per day in a sterile injectable formulation. The desired dose may be administered as two, three or more sub-doses at appropriate intervals, generally equally spread in time, throughout the day. Preferably, the full daily dose is administered in one administration.

Alternatively, Product R may be administered to the patients according to the conventional dosages or any dosages that are apparent to a person of ordinary skill in the art.

Product R may be administered by any suitable injection route including, but not limited to intravenously, intraperitoneally, subcutaneously, intramuscularly, and intradermally, etc. The presently preferred route of administration is intramuscularly. It will be appreciated that the preferred route may vary with, for example, the condition and age of the recipient.

Product R may be used in therapy in conjunction with other medicaments including corticosteroid, gamma globulin, glucose, or vitamins, antiviral agents such as interferon or interleukin, etc.

The present invention is further provide a method for treating patients suffering from non-solid tumors such as Lymphocytic Leukemias, Hodgkin's Disease and Non-Hodgkin's Lymphoma by administering the active components or active portion(s) of Product R to such patients. The active components or portions of Product R are described in the above mentioned U.S. Pat. Nos. 6,303,153 and 6,528,098.

While it is possible for Product R to be administered as part of a pharmaceutical formulation, it is preferable to present it alone, although it may be administered at about the same time as one or more other pharmaceuticals are independently administered. If Product R is administered as part of a pharmaceutical formulation, the formulations of the present invention comprise at least one administered ingredient, i.e. Product R, as above defined, together with one or more acceptable carriers thereof and optionally other therapeutic ingredients. The carrier(s) must be "acceptable" in the sense of being compatible with the other ingredients of the formulation and not deleterious to the recipient thereof.

The formulations may conveniently be presented in unit-dose or multi-dose containers, e.g. sealed ampules and vials.

Preferred unit dosage formulations are those containing a daily dose or unit, daily sub-dose, or an appropriate fraction of the administered ingredient.

In patients with cancer of lymphocytic cells such as acute lymphocytic leukemia, Hodgkin's lymphoma and non-Hodgkin's lymphoma, patients have been treated initially with 2 ml of Product R administered subcutaneously in equally divided doses in the morning and the evening for 2-4 weeks and then with 1 ml of Product R per day. There were no toxic reactions observed with Product R therapy. The treatment with Product R usually resulted in the shrinkage of enlarged lymph nodes in patients with Hodgkin's disease or Non-Hodgkin's lymphoma with Product R, and the shrinkage of an enlarged spleen in such patients.

The following examples only serves to further illustrate, but not to limit the scope of the present invention.

EXAMPLE 1

In a 71 year old white male with acute lymphocytic leukemia who failed intensive courses of conventional chemotherapy, Product R was effective in keeping this patient alive for 18 months. Chemotherapy was discontinued soon after commencing Product R therapy. Indeed, after commencing Product R therapy the patient's bone marrow which had contained 30% blast cells lost these blast cells. In addition, blast cells disappeared from the peripheral blood. During this two year period the patient put on weight, had a normal appetite, claimed that he felt well, and was able to live a normal quality of life. The patient died soon after a fall in his home.

EXAMPLE 2

Product R also proved effective in the treatment of a patient with stage 4B Hodgkin's disease. This patient had failed a stem cell transplant with recurrence of the Hodgkin's disease. The bone marrow was infiltrated with Hodgkin's tumor cells and there were large inguinal and para-aortic lymph nodes. Moreover, the spleen was markedly enlarged filling most of the abdomen and causing the patient pain. She was chronically fatigued and weak and was not able to work. After treatment with Product R she reported a return to normal activity and energy with increased appetite and strength after one week of therapy. She was able to return to work after a year's absence. Moreover, the peripheral lymph nodes disappeared and there was marked shrinkage of the spleen to a more normal size. This patient died due to a blood borne infection secondary to a infected an infected mediport catheter.

EXAMPLE 3

Method for Preparing Product R

Suspend about 35.0 g of casein, about 17.1 g of beef peptone, about 22.0 g of nucleic acid (RNA), about 3.25 g bovine serum albumin in about 2.5 liters of water for injection USP at about 3 to 7° C. in a suitable container and gently stir until all the ingredients have been properly wet. Carefully add while stirring about 16.5 g of sodium hydroxide (reagent grade ACS) and continue stirring until sodium hydroxide completely dissolved. Autoclave at about 9 lbs pressure and 200-230° F. for a period of time until RNA is completely digested, for example, about 4 hours. At the end of the period, the autoclave is stopped and the reaction flask and contents are permitted to slowly cool to ambient temperature. Then cool for at least six hours at about 3-8° C. The resulting solution is filtered through 2 micron and 0.45 micron filters using inert gas such as nitrogen or argon at low pressure (1-6 psi). In a similar manner the solution is filtered again through 0.2 micron pyrogen retention filters. The resulting filtrate is sampled and assayed for total nitrogen. A calculation is then performed to determine the quantity of cooled water for injection to be added to the filtrate to yield a diluted filtrate with a nitrogen content between about 165-210 mg/100 ml, the final volume is approximately 5 liters. The pH is then adjusted with either concentrated HCl (reagent grade ACS) or 1.0 normal NaOH to about 7.3-7.6 range. The diluted solution is then filtered again through 0.2 micron filters with inert gas at low pressure. The final filtrate is then filled and sealed into 2 ml glass ampules while in an inert gas atmosphere. The ampules are collected and autoclaved for final sterilization at 240° F. and 20 to 30 pounds pressure for about 30 minutes. Following the sterilization cycle, the ampules with Product R are cooled and washed.

All quantities are subject to plus or minus 2.5% variation for pH, volume, and analytical adjustments.

I claim:

1. A method of shrinking enlarged lymph nodes in patients with Hodgkin's disease or Non-Hodgkin's lymphoma, comprising parenterally administering to said patient an effective amount of Product R for shrinking lymph nodes in a pharmaceutically acceptable formulation.

2. The method of claim 1, wherein said Product R is administered in a range from about 2.5 microliters to about 40 microliters per kilogram of body weight per day in a pharmaceutically acceptable formulation.

3. The method of claim 1, wherein said Product R is administered in an amount of 2 ml per day for about 2-4 weeks and subsequently 1 ml per day.

4. A method of shrinking enlarged spleen in patients with Hodgkin's disease or Non-Hodgkin's lymphoma, comprising parenterally administering to said patient an effective amount of Product R for shrinking spleen in a pharmaceutically acceptable formulation.

5. The method of claim 4, wherein said Product R is administered in a range from about 2.5 microliters to about 40 microliters per kilogram of body weight per day in a pharmaceutically acceptable formulation.

6. The method of claim 4, wherein said Product R is administered in an amount of 2 ml per day for about 2-4 weeks and subsequently 1 ml per day.

7. A method of treating body wasting, loss of appetite and fatigue in patients suffering from acute lymphocytic leukemia, chronic lymphocytic leukemia, Hodgkin's disease and non-Hodgkin's lymphoma, comprising parenterally adminstereing to said patient an effective amount of Product R in a pharmaceutically acceptable formulation.

8. The method of claim 7, wherein said Product R is administered in a range from about 2.5 microliters to about 40 microliters per kilogram of body weight per day in a pharmaceutically acceptable formulation.

9. The method of claim 7, wherein said Product R is administered in an amount of 2 ml per day for about 2-4 weeks and subsequently 1 ml per day.

* * * * *